(12) United States Patent
Hung et al.

(10) Patent No.: US 10,500,099 B2
(45) Date of Patent: Dec. 10, 2019

(54) LONG-TERM EFFECTIVE PATCH STRUCTURE

(71) Applicant: Sigknow Biomedical Corporation Limited, New Taipei (TW)

(72) Inventors: Ming-Wei Hung, New Taipei (TW); Yi-Yuan Chiu, New Taipei (TW)

(73) Assignee: Sigknow Biomedical Corporation Limited, New Taipei (TW)

(*) Notice: Subject to any disclaimer, the term of this patent is extended or adjusted under 35 U.S.C. 154(b) by 696 days.

(21) Appl. No.: 14/970,067

(22) Filed: Dec. 15, 2015

(65) Prior Publication Data

US 2016/0166439 A1  Jun. 16, 2016

(30) Foreign Application Priority Data

Dec. 16, 2014 (TW) .............................. 103143920 A

(51) Int. Cl.
*A61F 13/00* (2006.01)
*A61F 13/02* (2006.01)

(52) U.S. Cl.
CPC ........ *A61F 13/022* (2013.01); *A61F 13/0206* (2013.01); *A61F 13/0226* (2013.01);
(Continued)

(58) Field of Classification Search
CPC ............. A61F 13/022; A61F 13/0206; A61F 13/0226; A61F 2013/0243; A61F 2013/00255; A61F 2013/00348; A61F 13/02; A61F 13/0246; A61F 2013/00889; A61F 2013/00442; A61F 2013/00655; A61F 2013/00676; A61F 2013/00731; A61F 2013/00761; A61F 2013/00885; A61F 2013/00961; A61F 13/0203; A61F 13/0209; A61F 13/0213; A61B 5/0432; A61B 5/683; A61N 1/0468; A61N 1/205; A61K 2300/00; A61K 33/24; A61K 33/40; A61K 31/59; A61K 33/00; A61K 9/0014; A61K 9/14; A61K 38/063; A61K 47/10;
(Continued)

(56) References Cited

U.S. PATENT DOCUMENTS 3,085,577 A * 4/1963 Berman ............... A61B 5/0416
600/392
4,166,465 A * 9/1979 Esty ....................... A61B 18/16
606/32
(Continued)

*Primary Examiner* — Kim M Lewis
(74) *Attorney, Agent, or Firm* — Wang Law Firm, Inc.

(57) ABSTRACT

A long-term effective patch structure includes a binding layer, an absorbing layer and a water-proof layer sequentially stacked together. The binding layer has a function of attaching and fixing, and is configured to be attached and fixed on a skin. Sweat or liquid from the skin can pass through the binding layer to reach the absorbing layer, which is aligned with binding layer at the edge. The water-proof layer is water-proof and has vapor permeability, and its area is larger than the area of the absorbing layer. The outer part of the water-proof layer is attachable to the skin. Since the absorbing layer can absorb the liquid from the skin and the water-proof layer can ventilate the vapor to the outside, the skin is kept dry and comfortable and suitable to be attached to human skin for a long period of time without inducing skin allergy or discomfort.

4 Claims, 4 Drawing Sheets

(52) U.S. Cl.
CPC ............... *A61F 13/0243* (2013.01); *A61F 2013/00255* (2013.01); *A61F 2013/00348* (2013.01)

(58) Field of Classification Search
CPC ........ A61K 8/0208; A61K 8/345; A61K 8/37; A61K 8/64; A61K 9/7023; A61K 9/7084; A61K 2800/42; A61K 2800/72; A61K 31/198; A61K 31/30; A61K 31/4995; A61K 31/785; A61K 31/795; A61K 33/34; A61K 33/38; A61K 41/0047; A61K 45/06; A61K 47/34; A61K 47/38; A61K 49/223; A61K 8/0212; A61K 8/19; A61K 8/368; A61K 8/39; A61K 8/46; A61K 8/498; A61K 8/4986; A61K 8/553; A61K 8/67; A61K 8/676; A61K 8/73; A61K 8/8176; A61K 8/891; A61K 8/922; A61K 8/9783; A61K 8/99; A61K 9/0017; A61K 9/0024; A61K 9/0031; A61K 9/0034; A61K 9/0043; A61K 9/0053; A61K 9/06; A61K 9/12; A61K 9/7061; A61K 9/7076
USPC ........ 600/372, 386, 391, 392; 607/152, 149; D24/189
See application file for complete search history.

(56) References Cited

U.S. PATENT DOCUMENTS

| | | | | |
|---|---|---|---|---|
| 4,832,036 A * | 5/1989 | Cartmell | ............ | A61B 5/04087 600/396 |
| 4,928,681 A * | 5/1990 | Langston | ............ | A61F 13/00029 602/58 |
| 5,012,810 A * | 5/1991 | Strand | ............ | A61B 5/04087 600/391 |
| 5,218,973 A * | 6/1993 | Weaver | ............ | A61B 5/0408 607/152 |
| 5,973,221 A * | 10/1999 | Collyer | ............ | A61F 13/00034 602/46 |
| 5,998,694 A * | 12/1999 | Jensen | ............ | A61F 13/023 602/43 |
| 6,103,951 A * | 8/2000 | Freeman | ............ | A61F 13/0206 602/43 |
| 7,220,889 B2 * | 5/2007 | Sigurjonsson | ...... | A61F 13/0203 602/41 |
| 2005/0182347 A1 * | 8/2005 | Bishop | ............ | A61F 13/022 602/43 |
| 2006/0020235 A1 * | 1/2006 | Siniaguine | ........ | A61F 13/00995 602/41 |
| 2008/0171957 A1 * | 7/2008 | Connolly | ............ | A61B 5/0531 602/42 |
| 2009/0287133 A1 * | 11/2009 | LaGreca, Sr. | ..... | A61F 13/00063 602/54 |
| 2011/0054429 A1 * | 3/2011 | Lademann | ............ | A61F 13/0203 604/361 |
| 2011/0144470 A1 * | 6/2011 | Mazar | ............ | A61B 5/04085 600/391 |
| 2012/0310070 A1 * | 12/2012 | Kumar | ............ | A61B 5/6833 600/391 |
| 2013/0018249 A1 * | 1/2013 | Storm | ............ | A61B 5/04085 600/384 |
| 2013/0053747 A1 * | 2/2013 | Lin | ............ | A61F 13/0209 602/45 |
| 2013/0281951 A1 * | 10/2013 | Ferris | ............ | A61F 13/538 604/368 |
| 2014/0121649 A1 * | 5/2014 | Calco | ............ | A61F 13/0206 604/543 |
| 2014/0128688 A1 * | 5/2014 | Wu | ............ | A61B 5/0245 600/301 |
| 2015/0342526 A1 * | 12/2015 | Totman | ............ | A61N 1/046 600/391 |

* cited by examiner

LONG-TERM EFFECTIVE PATCH STRUCTURE

CROSS-REFERENCE TO RELATED APPLICATION

This application claims the priority of Taiwan patent application No. 103143920, filed on Dec. 16, 2014, which is incorporated herewith by reference.

BACKGROUND OF THE INVENTION

1. Field of the Invention

The present invention generally relates to a long-term effective patch structure, and more specifically to a long-term effective patch structure implemented by a three layers structure of a binding layer, an absorbing layer and a water-proof layer sequentially stacked together for absorbing liquid on the human skin to evaporate, penetrate and dissipate outside so as to keep dry and comfortable and provide isolation and protection.

2. The Prior Arts

Traditionally, wounded tissue is often covered by a covering like gauze, cotton sheet or cotton pad to keep clean and avoid infection due to external pollutant so as to fast recover. However, the covering is removed while the user needs to replace the medicine on the wounded tissue. It is possible to cause secondary damage because the new tissue born in the wound is also peeled off and recovery seriously slows down.

In the prior arts, hydrophilic patch material like carboxymethyl cellulose (CMC), hydrogel, foam and alginate fiber is used to provide better care for the wound and solve the problem of secondary damage. However, one shortcoming in the prior arts is that the above hydrophilic patch material is easily and broken to pieces because of absorbing too much liquid and swelling when covering the wound with high seeping liquid. As a result, it is possible for the remaining pieces of the hydrophilic patch material on the skin to infect the wound. In addition, the hydrophilic patch material used to cover the wound with less or no seeping liquid also needs to replace in a short time due to the strong absorbing property. Obviously, it leads to inconvenience in actual application and a waste of the material.

Therefore, it is greatly needed to provide a new a long-term effective patch structure with a three layers structure generally comprising a binding layer, an absorbing layer and a water-proof layer sequentially stacked together. The binding layer attaches the skin, and the absorbing is used to absorb any liquid penetrating the binding layer from the skin. The water-proof layer covers and protects the binding layer and the absorbing layer, and also cause the liquid to evaporate and dissipate to the outside so as to keep dry and comfortable, thereby overcoming the above problems in the prior arts.

SUMMARY OF THE INVENTION

The primary objective of the present invention is to provide a long-term effective patch structure with a three layers structure generally comprising a binding layer, an absorbing layer and a water-proof layer sequentially stacked together. The present invention is suitable to directly attach to human skin for a long period of time so as to absorb liquid from the skin and keep dry and comfortable. Also, the long-term effective patch structure is specifically configured to combine a long term operation medical device or wearable device to form an integrated patch with desired medical function. As a result, it is effective to prevent skin from allergy, inflammation or any uncomfortable/irritating feeling.

The binding layer has a function of attaching and fixing and is configured to be directly attached and fixed on a skin for any liquid on the skin to penetrate. The absorbing layer absorbs the liquid from the binding layer. The water-proof layer is formed of water-proof coating or film, and has an area larger than an area of the absorbing layer such that the outer portion of the water-proof layer can be used to attach the skin for further enhancing the fixing effect.

In addition, the water-proof layer not only provides insulation to block any liquid, but also has high vapor permeability so as to evaporate and transfer the liquid absorbed by the absorbing layer through the water-proof layer to the outside. The skin is thus kept the dry and comfortable. In particular, the present invention is suitably applicable to a wound to providing cleaner and less humid environment for fast recovery.

The present invention may further comprise at least one of a conductive electrode layer and a release layer. The conductive electrode layer is configured between the binding layer and the absorbing layer to provide a measuring function for physiological signal from the skin, such as electrocardiography (ECG), electromyograph (EMG) and electroencephalogram (EEG). The release layer is provided on the water-proof layer, and has an area larger than the area of the water-proof layer so as to protect the binding layer and the water-proof layer. The user may remove the release layer to use the long-term effective patch structure.

Another object of the present invention is to provide a long-term effective patch structure comprising a binding layer, an absorbing layer and a water-proof layer, wherein the binding layer has a function of attaching and fixing, and is configured to be attached and fixed on the human skin, and the absorbing layer can attach the skin to absorb liquid from the skin. In particular, the binding layer and the absorbing layer are configured not to mutually stack or interfere with each other. Therefore, the present invention can also provide the function of absorbing liquid on the skin and greatly enhancing dissipation of the liquid to the outside, thereby keeping the skin dry and comfortable.

Moreover, the present invention further comprises a reinforcing layer specifically provided on the binding layer and the absorbing layer so as to reinforce strength of the whole structure. The reinforcing layer has hardness larger than hardness of the water-proof layer, the binding layer and the absorbing layer, wherein the reinforcing layer has an area smaller than the area of the water-proof layer.

The absorbing layer may further comprise a rigid base used to support a long term medical device or wearable device, and particularly, the rigid base has an area smaller than the area of the water-proof layer.

Therefore, the above long-term effective patch structure of the present invention can combine with a long term medical device or wearable device configured on the human body to provide specific medical function, like blood glucose meter, electrocardiogram machine, heartbeat detector, respiration detector, sphygmomanometer or medicine releasing device, which is needed to wear for a long period of time to achieve long term monitoring for physiological status. As a result, the user simply configures the long term medical device or wearable device to the long-term effective patch structure to implement the original function for the long term medical device or wearable device, thereby greatly improving convenience in application.

BRIEF DESCRIPTION OF THE DRAWINGS

The present invention will be apparent to those skilled in the art by reading the following detailed description of a preferred embodiment thereof, with reference to the attached drawings, in which.

DETAILED DESCRIPTION OF THE PREFERRED EMBODIMENT

The accompanying drawings are included to provide a further understanding of the invention, and are incorporated in and constitute a part of this specification. The drawings illustrate embodiments of the invention and, together with the description, serve to explain the principles of the invention.

Figure 1:
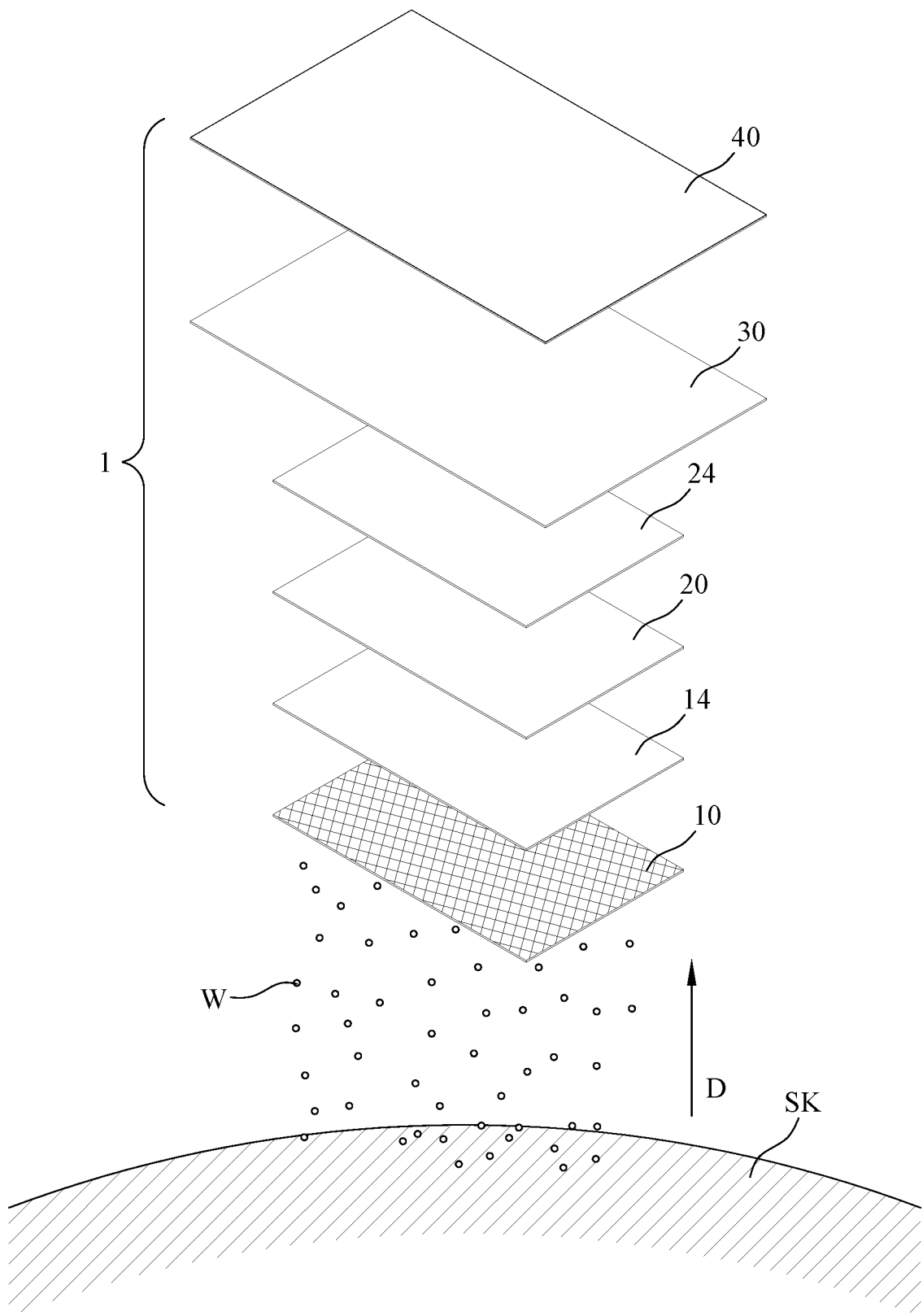
FIG. 1 is a perspective view showing the long-term effective patch structure according to one embodiment of the present invention.
Figure 2:
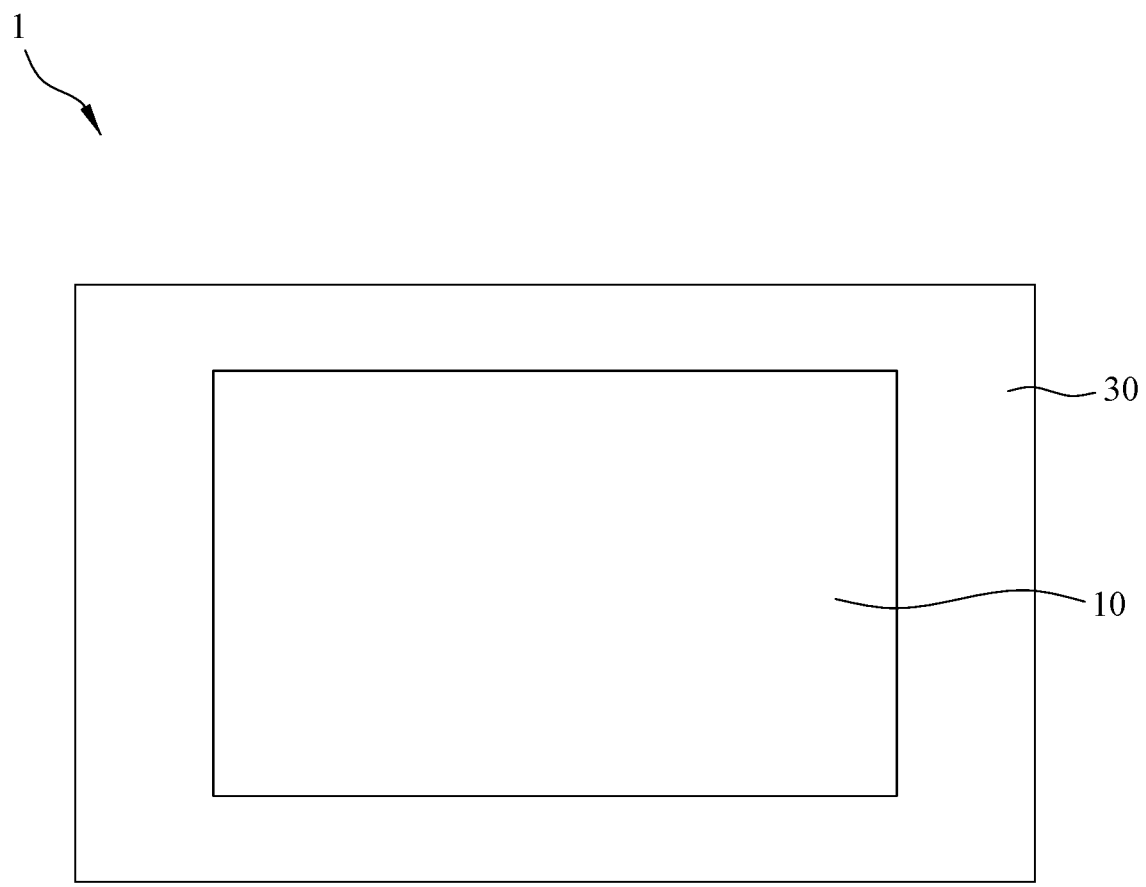
FIG. 2 is a bottom view showing the long-term effective patch structure in FIG. 1.

Please refer to FIGS. 1 and 2 illustrating the perspective and bottom views of the long-term effective patch structure according to the embodiment of the present invention, respectively. As shown in FIGS. 1 and 2, the long-term effective patch structure 1 according to one embodiment of the present invention generally comprises a binding layer 10, an absorbing layer 20 and a water-proof layer 30 for directly attaching to the human skin SK so as to absorb liquid W from the skin SK such as sweat or tissue liquid entering in a direction D, such that the liquid W absorbed gradually and readily evaporates and the skin SK is kept dry and comfortable. Thus, the long-term effective patch structure 1 of the present embodiment can attach to the skin SK for at least 7 to 14 days without causing any irritating/uncomfortable feeling or allergy.

Specifically, the binding layer 10 has a function of attaching and fixing and is configured to be directly attached and fixed on the skin SK. The absorbing layer 20 is stacked on the binding layer 10 to absorb any liquid W from the binding layer 10 and the skin SK, and particularly, the absorbing layer 20 is aligned with binding layer 10 at the edge. In other words, the binding layer 10 and the absorbing layer 20 have the same shape and area in the horizontal surface.

The binding layer 10 absorbs the liquid W from the skin SK to cause the liquid W to easily penetrate and reach the absorbing layer 20. The water-proof layer 30 is stacked on the absorbing layer 20, and has an area larger than an area of the absorbing layer 20 such that the absorbing layer 20 is covered by the water-proof layer 30, and the portion of water-proof layer 30 not covering the absorbing layer 20 is used to attach the skin SK. Particularly, the water-proof layer 30 has a size extending from an outermost edge of the absorbing layer 20 by at least 2 mm.

It is preferred that the absorbing layer 20 is implemented by acrylic, polyurethane (PU), silicone, hydrogel, artificial skin, non-woven cloth, resin, cotton, polymer or plastic material.

Additionally, the water-proof layer 30 is formed of a water-proof coating or a water-proof film, and further provides the water-proof effect to insulate and block any external liquid from entering the absorbing layer 20, and has high moisture vapor transmission rate (MVTR) so as to cause the liquid W absorbed to evaporate and transfer to the outside, thereby keeping the skin SK in a dry and comfortable status.

More specifically, the binding layer 10 is implemented by acrylic, PU, silicone, hydrogel or artificial skin, and has a structure of through holes, network or gaps for sweat or tissue liquid from the skin to pass through the binding layer 10 and reach the absorbing layer 20, which absorbs the liquid.

The long-term effective patch structure 1 of the present embodiment further comprises another water-proof layer 14, which is sandwiched between the binding layer 10 and the absorbing layer 20, and implemented by a water-proof coating or a water-proof film with a structure of through holes, network or gaps. The above another water-proof layer 14 prevents the absorbing layer 20 from absorbing the liquid W absorbed by the binding layer 10 during the long-term effective patch structure 1 is manufactured.

In addition, the present invention may further comprise a conductive electrode layer 24 and/or a releasing layer 40. The conductive electrode layer 24 is formed of metal or any conductive material, and is configured between the binding layer 10 and the absorbing layer 20, and/or the absorbing layer 20 and the water-proof layer 30 for providing a function to measure physiological signal of the human body, such as ECG, EMG and EEG. The release layer 40 is provided on the water-proof layer 30, and has an area larger than the area of the water-proof layer 30 so as to protect the binding layer 10 and the water-proof layer 30. The user needs to remove the release layer 40 only when the long-term effective patch structure 1 is used for attaching.

Figure 3:
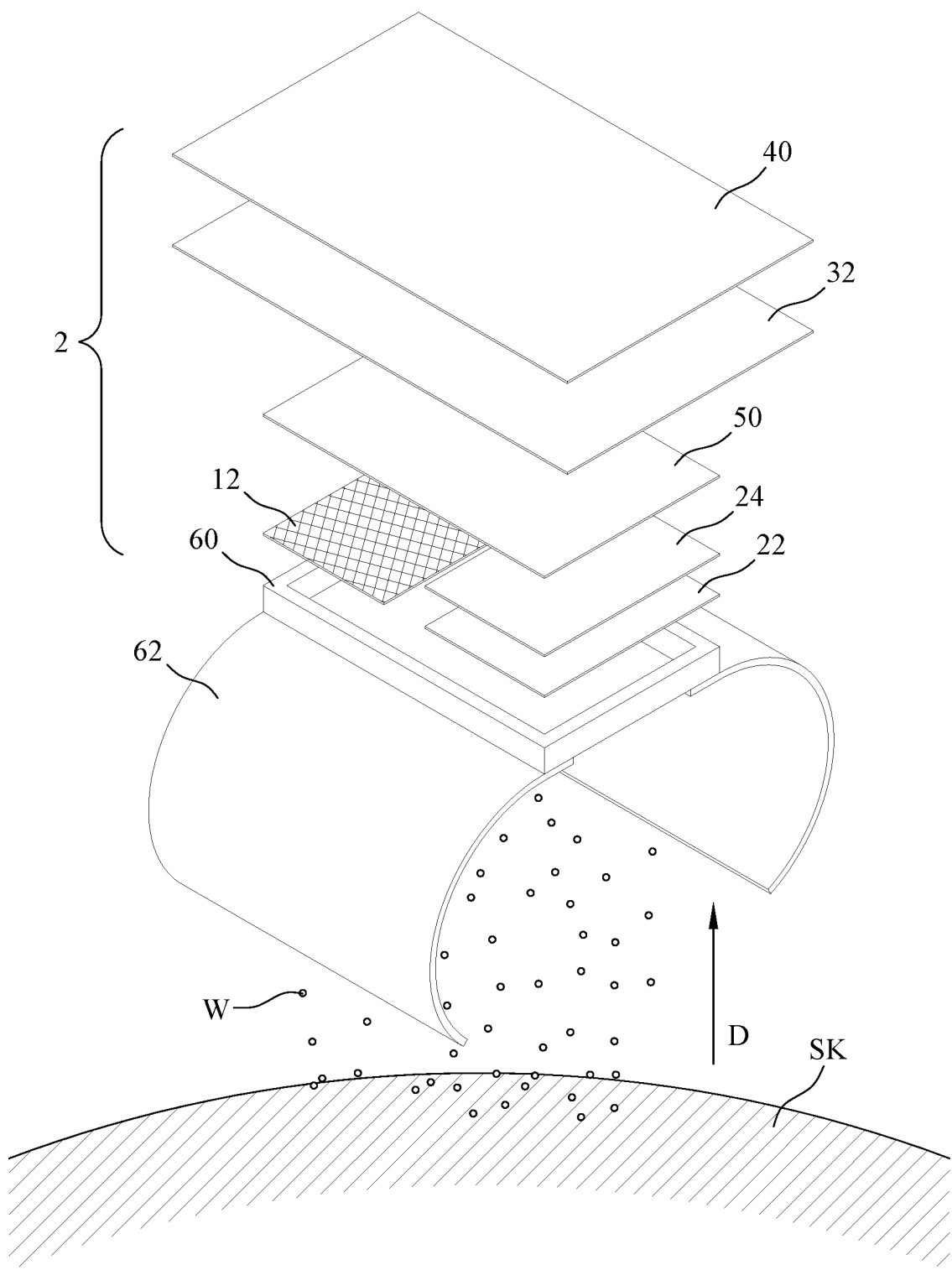
FIG. 3 is a perspective view showing the long-term effective patch structure according to another embodiment of the present invention.
Figure 4:
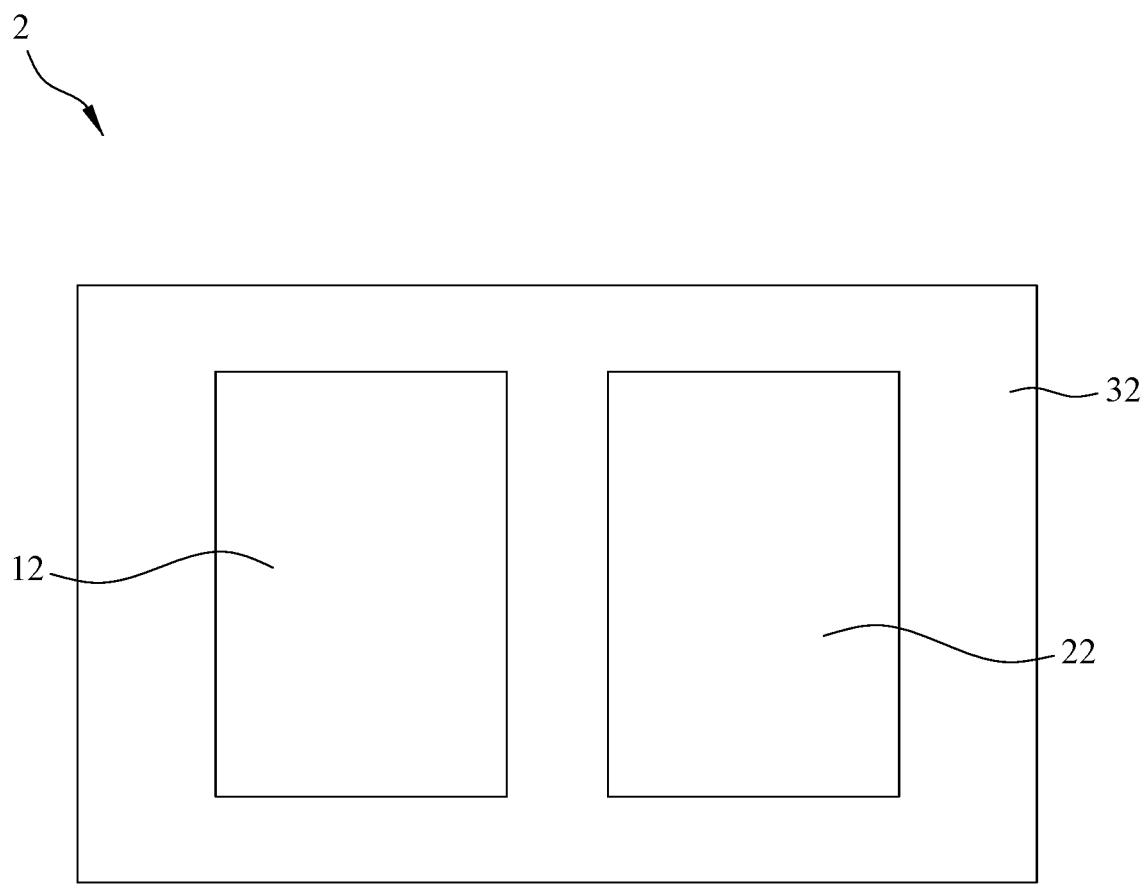
FIG. 4 is a bottom view showing the long-term effective patch structure in FIG. 3.

Further refer to FIGS. 3 and 4 illustrating the perspective and bottom views of the long-term effective patch structure according to another embodiment of the present invention, respectively.

As shown in FIGS. 3 and 4, the long-term effective patch structure 2 comprises the binding layer 12, the absorbing layer 22 and the water-proof layer 32. It should be noted that the present embodiment is similar to the embodiment shown in FIGS. 1 and 2. The primary difference is that the binding layer 12 and the absorbing layer 22 in FIGS. 3 and 4 are not stacked together, but respectively attached to the same surface of the water-proof layer 32, like the lower surface of the water-proof layer 32. Thus, the binding layer 12 has the attaching and fixing feature, and is attachable to the skin SK. The absorbing layer 22 can be also attached to the skin SK to absorb the liquid W. Particularly, the binding layer 12 and the absorbing layer 22 are configured not to mutually stack together or interfere with each other. Since other elements in FIGS. 3 and 4 are similar to those FIGS. 1 and 2, the detailed description is omitted hereinafter.

Moreover, the present embodiment further comprises a reinforcing layer 50, which is provided on the lower surface of the water-proof layer 32 and between the binding layer 12 and the absorbing layer 22. In other words, the binding layer 12 and the absorbing layer 22 is attached to the lower surface of the reinforcing layer 50, and the upper surface of the reinforcing layer 50 is attached to the lower surface of the water-proof layer 32. More specifically, the reinforcing layer 50 has hardness larger than hardness of the water-proof layer 32, the binding layer 12 and the absorbing layer 22 to as to enhance strength of the whole structure. Preferably, the reinforcing layer 50 has an area smaller than the area of the water-proof layer 32.

The long-term effective patch structure 2 of the present embodiment may also comprise at least one of a conductive electrode layer and a release layer 40. The conductive electrode layer 24 is used to measure physiological signal from the skin, and specifically configured between the binding layer 12 and the absorbing layer 22 such that the conductive electrode layer 24 directly or indirectly contacts the human skin SK to measure the physiological signal. The release layer 40 is provided on the water-proof layer 32, and has an area larger than the area of the water-proof layer 32. Additionally, a number of conductive electrode layers and the binding layer 12 are assembled and provided beneath the water-proof layer 32 so as to easily measure physiological signal such as ECG.

Also, the absorbing layer 22 further comprises a rigid base 60 for supporting a long term medical device or wearable device 62. In particular, the rigid base 60 has an area smaller than the area of the water-proof layer 32.

Overall, the long-term effective patch structure of the present invention can also provide the specific medical function of the long term medical device or wearable device 62 like blood glucose meter, electrocardiogram machine, heartbeat detector, respiration detector, sphygmomanometer or medicine releasing device, if the present invention is combined with the long term medical device or wearable device 62, and configured on the human body. As a result, the user simply configures the long term medical device or wearable device 62 to the long-term effective patch structure to demonstrate the original preset functions for the long term medical device or wearable device 62.

From the above mention, one of the primary aspects of the present invention is that the long-term effective patch structure formed as a three layers structure comprising the binding layer, the absorbing layer and the water-proof layer sequentially stacked together can be continuously attached to the skin for at least 7 to 14 days, and provides the advantage of water-proof without causing allergy or inflammation. Particularly, the present invent fast absorbs sweat or tissue liquid to keep the skin dry and comfortable. High vapor permeability is also provided to readily evaporate and transfer the liquid absorbed by the absorbing layer through the water-proof layer to the outside. Thus, the present invention is suitable to cover the region of the skin with a wound so as to provide excellent care and insulation and prevents the wound from badly humid environment, thereby greatly speeding up recovery.

Another aspect of the present invention is that the area of the water-proof layer is larger than the absorbing layer and the binding layer, and its outer portion can be attached to the skin so as to fix all the stack structure and cover the skin. At the same time, any external water is effectively prevented from entering the absorbing layer and the binding layer to maintain the sticky property for attaching.

Although the present invention has been described with reference to the preferred embodiments thereof, it is apparent to those skilled in the art that a variety of modifications and changes may be made without departing from the scope of the present invention which is intended to be defined by the appended claims.

What is claimed is:

1. A long-term effective patch structure, comprising:
 a binding layer having a function of attaching and fixing, and being configured to be attached and fixed on a human skin;
 an absorbing layer for absorbing liquid from the skin or the binding layer, the binding layer and the absorbing layer being configured not to mutually stack or interfere with each other;
 a water-proof layer configured to be on the binding layer and the absorbing layer and having an area larger than a total area of the binding layer and the absorbing layer,
 wherein the absorbing layer is covered by the water-proof layer, an outer part of the water-proof layer not covering the absorbing layer is used to attach to the skin, the water-proof layer provides a water-proof function to insulate and block external liquid from entering the absorbing layer, and has high moisture vapor transmission rate (MVTR), and the water-proof layer has a thickness smaller than a thickness of the binding layer and a thickness of the absorbing layer; and
 further comprising at least one of a conductive electrode layer and a release layer, wherein the conductive electrode layer provides a function to measure electrocardiogram signal from the skin, and is configured between the binding layer and the absorbing layer such that the conductive electrode layer directly or indirectly contacts the human skin to measure the electrocardiogram signal, and the release layer is provided on the water-proof layer, and has an area larger than the area of the water-proof layer.

2. The long-term effective patch structure as claimed in claim 1, wherein the binding layer is implemented by acrylic, polyurethane (PU), silicone, hydrogel or artificial skin, and has a structure of through holes, network or gaps for sweat or tissue liquid from the skin to pass through the binding layer and not to remain between the human skin and the binding layer, the sweat or tissue liquid gradually evaporates through the water-proof layer over time, the absorbing layer is implemented by acrylic, polyurethane, silicone, hydrogel, artificial skin, non-woven cloth, resin, cotton, polymer or plastic material, and the water-proof layer is stacked on the absorbing layer, and has a size extending from an outermost edge of the absorbing layer by 2~3 mm.

3. The long-term effective patch structure as claimed in claim 1, further comprising a reinforcing layer provided on the absorbing layer for reinforcing strength, wherein the reinforcing layer has hardness larger than hardness of the water-proof layer, the binding layer and the absorbing layer, and the reinforcing layer has an area smaller than the area of the water-proof layer.

4. The long-term effective patch structure as claimed in claim 1, wherein the absorbing layer further comprises a rigid base for supporting a long term medical device or wearable device, and the rigid base has an area smaller than the area of the water-proof layer.

* * * * *